United States Patent [19]

Barfurth et al.

[11] 4,313,851
[45] Feb. 2, 1982

[54] LIQUID, COLD-STABLE TITANIUM CATALYST PREPARATION

[75] Inventors: Dieter Barfurth, Lohmar; Heinz Nestler, Troisdorf-Eschmar, both of Fed. Rep. of Germany

[73] Assignee: Dynamit Nobel AG, Troisdorf, Fed. Rep. of Germany

[21] Appl. No.: 239,915

[22] Filed: Mar. 2, 1981

[51] Int. Cl.$^3$ .............................................. B01J 31/12
[52] U.S. Cl. ............................. 252/431 R; 260/429 R
[58] Field of Search ................ 252/431 R; 260/429 R

[56] References Cited
PUBLICATIONS

A. Yamamoto et al., "Structures of the Reaction Products of Tetraalkoxytitanium with Acetylacetone and Ethyl Acetoacetate", J. Am. Chem. Soc. 79 (1957), 4344–4348.

*Primary Examiner*—Jacqueline V. Howard
*Attorney, Agent, or Firm*—Sprung, Felfe, Horn, Lynch & Kramer

[57] ABSTRACT

A cold-stable catalytically active solution of diisopropoxy-bis (2,4-pentanedionato)-titanium(IV) in isopropanol, said solution containing 0.05 to 0.15 mol of water per mol of said titanium compound.

5 Claims, No Drawings

LIQUID, COLD-STABLE TITANIUM CATALYST PREPARATION

BACKGROUND OF THE INVENTION

1. Field of the Invention

The subject matter of the present invention is a solution of diisopropoxy-bis (2,4-pentanedionato)-titanium (IV) in isopropanol, which is stable even at temperatures down to −20° C. and a process for preparing the same.

DISCUSSION OF PRIOR ART

Diisopropoxy-bis(2,4-pentanedionato)-titanium (IV) is in itself a known compound, which is used, for example, as a crosslinking agent, adhesivizer or catalyst. It differs from the tetraalkoxytitanates especially by its lower reactivity, which is often desirable, and by the fact that its hydrolysis takes place step-wise and initially only the alkoxy groups are liberated (with the formation of a titanyl compound) as isopropanol (cf. A. Yamamoto, S. Kambara, J. Am. Chem. Soc. 79 (1957), 4344–4348). To enable diisopropoxy-bis(2,4-pentanedionato)-titanium(IV), which in pure form is an orange-colored solid (cf. D. M. Puri et al., J. Less-Common Metals, 4 (1962), 393–398), to be handled more easily as a catalyst or crosslinking agent, its isopropanolic solution is, as a rule, used as it is produced by the conventional method of preparation by the reaction of tetraisopropyltitanate with acetylacetone in a molar ratio of 1:2. The term, titanium acetylacetonate, is commonly used to refer to this solution, which generally is composed of 75.2% of titanium compound and 24.8% of isopropanol by weight. In the known applications of this catalyst solution, the alcohol does not interfere, or it is removed by distillation and replaced by another solvent before the titanium compound is used.

During the cold season of the year, the following disadvantages are encountered in the storage, pumping and proportioning of this catalyst preparation; solid precipitates settle from time to time in the barrels, pipes and proportioning apparatus. These precipitates can be eliminated by heating, but this calls for an unnecessarily great amount of time and additional handling and costs. At the same time, the redissolution may cause undesirable differences of concentration, especially in barrels.

An attempt has already been made to forestall these undesirable phenomena by the addition of more isopropanol, other alcohols or other solvents. It was found, however, that when experimental mixtures were let stand at a test temperature of −20° C., many diluents proved to be ineffective even in relatively large amounts, and the formation of precipitates could not be prevented at low temperatures. In the case of many solvents, such as methanol or ethanol, for example, the use of amounts of at least 10% of the starting mixture did result in shelf lives of more than twenty weeks at −20° C. Such high proportions, however, mean that the alcohol content of the starting mixture increases from 24.8% to 31.6%, and the titanium content, expressed as titanium dioxide, diminishes from the original 16.5% $TiO_2$ to approximately 15% $TiO_2$. This, however, constitutes a rather great and undesirable modification of the product.

SUMMARY OF THE INVENTION

The problem, therefore, existed of stabilizing solutions of diisopropoxy-bis (2,4-pentanedionato)-titanium (IV) in isopropanol such that no precipitate forms even at temperatures down to −20° C., and that the titanium content of the solution is not significantly reduced by the stabilizing agent.

As the solution to this problem it has now been found that the addition of a precisely defined, small amount of water, namely 0.05 to 0.15 mol of water per mol of titanium atom cold-stabilizes titanium acetylacetonate solutions. Titanium acetylacetonate solutions treated in this manner have proven to be absolutely stable in long-term storage at −20° C., and they remain clear.

This invention, therefore, provides a solution of diisopropoxy-bis (2,4-pentandionato)-titanium (IV) in isopropanol which contains 0.05 to 0.15 mol of water per titanium atom. These solutions are stable at −20° C. for at least 12 months ... precipitates do not form at −20° C. when the same is stored for such period of time. The concentration of titanium expressed in terms of the oxide can be 16.4 to 16.5 weight percent.

The properties and effectiveness of the solution of the invention are virtually unaltered in comparison with the water-free solution. The addition of 0.1 mol of water per titanium atom does increase the alcohol content of the mixture by 2.5%, but the titanium content, expressed as $TiO_2$, decreases, however, only from 16.51 to 16.45%. Water additions below the limit stated above manifest a decidedly diminished effect; amounts greater than stated result in early precipitation even at room temperature.

The stabilizing action of the water added in accordance with the invention appears not only in the case of 75% titanium acetylacetonate solutions in isopropanol, but also in the case of solutions in which the content of the titanium compound varies between 65 and 80%, i.e., in catalyst solutions having an active $TiO_2$ content between about 14.3 and 17.6%.

The preparation of the cold-stable catalyst solutions in accordance with the invention can be accomplished easily by simple methods. In one method, the required amount of water is added during the preparation of the titanium acetylacetonate solutions, taking care that the entire amount of water does not react directly with the isopropylititanate placed in the reaction vessel. Therefore, it is desirable to mix the water with the acetylacetone before it is proportioned into the isopropyltitanate. Another method comprises adding the necessary amount of water to the prepared titanium acetylacetonate solution and heating the mixture for a period of time if necessary. Generally, the heating is effected at 50° to 90° C. for at least 10 minutes, preferably 30 to 120 minutes.

EXAMPLES

The following examples will serve to provide a further explanation of the method of preparing the products and testing them.

EXAMPLE 1

Preparation of the Catalyst Solution With Addition of Water 284 g (=1 mole) of isopropyltitanate is placed in a one-liter three-necked flask equipped with thermometer, stirrer and dropping funnel; a mixture of 200 g (=2 mol) of acetylacetone and 1.8 g (=0.1 mol) of water is proportioned through the dropping funnel such that a temperature of 60° C. is not exceeded in the reaction mixture. When the addition of the acetylacetone-water mixture is completed an orange-red liquid is obtained; the dropping funnel is replaced with a reflux condenser and this liquid is heated with refluxing for one hour to complete the reaction.

EXAMPLE 2

Modification of a Catalyst Solution by the Addition of Water 484 g of a commercial 75% titanium acetylacetonate solution in isopropanol is weighed into a one-liter round flask. This amount contains one mole of pure diisopropoxy-titanium-bis-acetylacetonate. To this is added 1.8 g (=0.1 mol) of water, which immediately dissolves therein. This mixture is then refluxed for one hour.

EXAMPLE 3

Testing of Crystallization at Low Temperatures

To test the tendency of the catalyst solutions to crystallize at temperatures below the freezing point of water, a sample of the material to be tested is placed in a deep-freeze compartment of a refrigerator. The temperature fluctuates at this location between −18° and −22° C. and averages −20° C.

The following table presents the results of the cold storage of the catalyst solutions with the addition of various amounts of water. The method of preparing the solutions is in accordance with Examples 1 and 2.

| Amount of water added in moles of $H_2O$ per atom of Ti | Crystallization Tendency at −20° C. | |
|---|---|---|
| | Preparation per Example 1 | Preparation per Example 2 |
| None | Crystallization occurs after 24 hours | |
| 0.025 mol/Ti | Crystallizes in 3 days | Crystallizes in 4 days |
| 0.05 mol/Ti | Still crystal-free after twelve months | Still crystal-free after twelve months |
| 0.10 mol/Ti | Still crystal-free after twelve months | Still crystal-free after twelve months |
| 0.15 mol/Ti | Still crystal-free after twelve months | Still crystal-free after twelve months |
| 0.20 mol/Ti | Precipitate forms after ten days at room temperature | Precipitate forms after 14 days at room temperature |

What is claimed is:

1. A cold-stable catalytically active solution of diisopropoxy-bis (2,4-pentanedionato)-titanium (IV) in isopropanol, said solution containing 0.05 to 0.15 mol of water per mol of said titanium compound.

2. A cold-stable catalytically active solution according to claim 1, which is cold-stable at −20° C. for at least 12 months.

3. A process for preparing the solution of claim 1, which comprises adding water during the preparation of diisopropoxy-bis (2,4-pentanedionato)-titanium (IV) solution when the same is prepared by a reaction of tetraisopropyl titanate and acetylacetone.

4. A method for preparing the catalyst solution of claim 1, which comprises adding 0.05 to 0.15 mol water per mol of diisopropoxy-bis (2,4-pentanedionato)-titanium (IV) solution which has been previously prepared.

5. A method according to claim 4, wherein said solution is a solution of said titanium compound in isopropanol.

* * * * *

UNITED STATES PATENT AND TRADEMARK OFFICE
CERTIFICATE OF CORRECTION

PATENT NO. : 4,313,851

DATED : Feb. 2, 1982

INVENTOR(S) : Dieter Barfurth et al

It is certified that error appears in the above-identified patent and that said Letters Patent are hereby corrected as shown below:

Title Page      Insert --Foreign Application Priority Data
March 4, 1980  Fed. Rep. of Germany....
3008193--.

Signed and Sealed this

Tenth Day of August 1982

[SEAL]

Attest:

GERALD J. MOSSINGHOFF

Attesting Officer        Commissioner of Patents and Trademarks